(12) United States Patent
D'Arcangelis et al.

(10) Patent No.: US 9,228,999 B2
(45) Date of Patent: Jan. 5, 2016

(54) METHOD FOR SCREENING ACTIVE AGENTS THAT STIMULATE THE EXPRESSION OF CERT TO IMPROVE THE SKIN'S BARRIER FUNCTION

(75) Inventors: Alexandra D'Arcangelis, Randolph, NJ (US); Elena Fedorova, Whippany, NJ (US)

(73) Assignee: CHANEL PARFUMS BEAUTE, Neuilly sur Seine (FR)

( * ) Notice: Subject to any disclaimer, the term of this patent is extended or adjusted under 35 U.S.C. 154(b) by 106 days.

(21) Appl. No.: 13/514,412

(22) PCT Filed: Dec. 3, 2010

(86) PCT No.: PCT/EP2010/068849
§ 371 (c)(1),
(2), (4) Date: Jun. 7, 2012

(87) PCT Pub. No.: WO2011/069913
PCT Pub. Date: Jun. 16, 2011

(65) Prior Publication Data
US 2012/0244545 A1    Sep. 27, 2012

Related U.S. Application Data

(60) Provisional application No. 61/267,152, filed on Dec. 7, 2009, provisional application No. 61/267,150, filed on Dec. 7, 2009.

(51) Int. Cl.
*C12Q 1/25* (2006.01)
*C12Q 1/68* (2006.01)
*G01N 33/50* (2006.01)
*A61K 8/97* (2006.01)
*A61Q 19/00* (2006.01)

(52) U.S. Cl.
CPC .............. *G01N 33/5044* (2013.01); *A61K 8/97* (2013.01); *A61Q 19/00* (2013.01); *C12Q 1/6883* (2013.01); *C12Q 1/6851* (2013.01); *C12Q 2600/136* (2013.01); *G01N 2800/20* (2013.01)

(58) Field of Classification Search
USPC ......................................................... 435/6.12
See application file for complete search history.

(56) References Cited

U.S. PATENT DOCUMENTS

| | | | |
|---|---|---|---|
| 6,124,364 A * | 9/2000 | Breton et al. | 514/733 |
| 6,649,362 B2 * | 11/2003 | Gamble et al. | 435/15 |
| 2004/0018218 A1 | 1/2004 | Philippe et al. | |
| 2005/0118283 A1 | 6/2005 | Calverley et al. | |
| 2006/0165632 A1 | 7/2006 | Mehul | |
| 2007/0071710 A1 | 3/2007 | Maestro et al. | |
| 2008/0085859 A1 | 4/2008 | Hanada et al. | |
| 2009/0035236 A1 | 2/2009 | Maes et al. | |

FOREIGN PATENT DOCUMENTS

| | | | |
|---|---|---|---|
| EP | 1 652 530 A1 | 5/2006 | |
| FR | 2 811 556 A1 | 1/2002 | |
| WO | 02/38110 A2 | 5/2002 | |
| WO | 2007/034042 A2 | 3/2007 | |
| WO | WO2008151891 * | 12/2008 | ............... A61K 8/97 |
| WO | 2009/077995 A1 | 6/2009 | |

OTHER PUBLICATIONS

Di Nardo A, Wertz P, Giannetti A, Seidenari S. Ceramide and cholesterol composition of the skin of patients with atopic dermatitis. Acta Derm Venereol. Jan. 1998;78(1):27-30.*
Granero-Moltó F, Sarmah S, O'Rear L, Spagnoli A, Abrahamson D, Saus J, Hudson BG, Knapik EW. Goodpasture antigen-binding protein and its spliced variant, ceramide transfer protein, have different functions in the modulation of apoptosis during zebrafish development. J Biol Chem. Jul. 18, 2008; 283(29):20495-504. Epub Apr. 18, 2008.*
Hanada K, Kumagai K, Tomishige N, Kawano M. CERT and intracellular trafficking of ceramide. Biochim Biophys Acta. Jun. 2007;1771(6):644-53. Epub Jan. 23, 2007. Review.*
Mizutani Y, Mitsutake S, Tsuji K, Kihara A, Igarashi Y. Ceramide biosynthesis in keratinocyte and its role in skin function. Biochimie. Jun. 2009;91(6):784-90. Epub Apr. 11, 2009. Review.*
Florin L, Pegel A, Becker E, Hausser A, Olayioye MA, Kaufmann H. Heterologous expression of the lipid transfer protein CERT increases therapeutic protein productivity of mammalian cells. J Biotechnol. Apr. 20, 2009;141(1-2):84-90. Epub Mar. 6, 2009.*
Yamaji T, Kumagai K, Tomishige N, Hanada K. Two sphingolipid transfer proteins, CERT and FAPP2: their roles in sphingolipid metabolism. IUBMB Life. Aug. 2008;60(8):511-8. Review.*
Jungersted JM, Hellgren LI, Jemec GB, Agner T. Lipids and skin barrier function—a clinical perspective. Contact Dermatitis. May 2008;58(5):255-62. Review.*
Revert F, Ventura I, Martinez-Martinez P, Granero-Moltó F, Revert-Ros F, Macias J, Saus J. Goodpasture antigen-binding protein is a soluble exportable protein that interacts with type IV collagen. Identification of novel membrane-bound isoforms. J Biol Chem. Oct. 31, 2008;283(44):30246-55. Epub Sep. 4, 2008.*
Perry RJ, Ridgway ND. Molecular mechanisms and regulation of ceramide transport. Biochim Biophys Acta. Jun. 1, 2005;1734(3):220-34. Review.*
Lee SH, Jeong SK, Ahn SK. An update of the defensive barrier function of skin. Yonsei Med J. Jun. 30, 2006; 47(3):293-306. Review.*

(Continued)

*Primary Examiner* — Samuel Woolwine
*Assistant Examiner* — Olayinka Oyeyemi
(74) *Attorney, Agent, or Firm* — Young & Thompson

(57) ABSTRACT

A method for screening an active agent intended for preventing or combating the cutaneous signs resulting from a non-pathological impairment of barrier function, which includes the selection of active agents that stimulate the expression of the ceramide transport protein CERT in cultured human keratinocytes.

5 Claims, No Drawings

(56) References Cited

OTHER PUBLICATIONS

Lee AJ, East P, Pepper S, Nicke B, Szallasi Z, Eklund AC, Downward J, Swanton C. Concordance of exon array and real-time PCR assessment of gene expression following cancer cell cytotoxic drug exposure. Cell Cycle. Dec. 15, 2008;7(24):3947-8. Epub Dec. 17, 2008.*
Swanton C, Marani M, Pardo O, Warne PH, Kelly G, Sahai E, Elustondo F, Chang J, Temple J, Ahmed AA, Brenton JD, Downward J, Nicke B. Regulators of mitotic arrest and ceramide metabolism are determinants of sensitivity to paclitaxel and other chemotherapeutic drugs. Cancer Cell. Jun. 2007; 11(6):498-512.*
Jensen JM, Fölster-Holst R, Baranowsky A, Schunck M, Winoto-Morbach S, Neumann C, Schütze S, Proksch E. Impaired sphingomyelinase activity and epidermal differentiation in atopic dermatitis. J Invest Dermatol. Jun. 2004;122(6):1423-31.*
Greenbaum D, Colangelo C, Williams K, Gerstein M. Comparing protein abundance and mRNA expression levels on a genomic scale. Genome Biol. 2003;4(9):117. Epub Aug. 29, 2003. Review.*
Cheung VG, Conlin LK, Weber TM, Arcaro M, Jen KY, Morley M, Spielman RS. Natural variation in human gene expression assessed in lymphoblastoid cells. Nat Genet. Mar. 2003;33(3):422-5. Epub Feb. 3, 2003.*
Saito-Hisaminato A, Katagiri T, Kakiuchi S, Nakamura T, Tsunoda T, Nakamura Y. Genome-wide profiling of gene expression in 29 normal human tissues with a cDNA microarray. DNA Res. Apr. 30, 2002;9(2):35-45.*
Hanada K, Kumagai K, Tomishige N, Kawano M. CERT and intracellular trafficking of ceramide. Biochim Biophys Acta. Jun. 2007; 1771(6):644-53. Epub Jan. 23, 2007.*
Gallala H, Macheleidt O, Doering T, Schreiner V, Sandhoff K. Nitric oxide regulates synthesis of gene products involved in keratinocyte differentiation and ceramide metabolism. Eur J Cell Biol. Dec. 2004; 83(11-12):667-79.*
Kumagai K, Kawano M, Shinkai-Ouchi F, Nishijima M, Hanada K. Interorganelle trafficking of ceramide is regulated by phosphorylation-dependent cooperativity between the PH and START domains of CERT. J Biol Chem. Jun. 15, 2007; 282(24):17758-66. Epub Apr. 18, 2007.*
Yasuda S, Kitagawa H, Ueno M, Ishitani H, Fukasawa M, Nishijima M, Kobayashi S, Hanada K. A novel inhibitor of ceramide trafficking from the endoplasmic reticulum to the site of sphingomyelin synthesis. J Biol Chem. Nov. 23, 2001; 276(47):43994-4002. Epub Sep. 6, 2001.*
Charruyer Alexandra et al: "Decreased ceramide transport protein (CERT) function alters sphingomyelin production following UVB irradiation.", The Journal of Biological Chemistry Jun. 13, 2008 LNKD-PUBMED:18411267. vol. 283. No. 24. Jun. 13, 2008. pp. 16682-16692. XP002622419. ISSN: 0021-9258 cited in the application.
Rao Raghavendra Pralhada et al: Il Cerami de transfer protein function is essential for normal oxidative stress response and lifespan. Proceedings of the National Academy of Sciences of the United States of America. vol. 104. No. 27. Jul. 2007. pp. 11364-11369. XP002622420. ISSN: 0027-8424 cited in the application.
Elbadawy H et al: "Expression of the START family of lipid trafficking proteins in HaCaT keratinocytes: evidence for a role for STARD5 in keratinocyte differentiation and cholesterol homeostasis". British Journal of Dermatology. vol. 162. No. 4. Apr. 2010. p. 929. XP002622421. & Annual Meeting of the British-Society-For-Investigative-Dermatology; Edinburgh. UK; Apr. 12-14, 2010.
Bissett et al: "Common cosmeceuticals". Clinics in Dermatology. J.B. Lippincott. Philadelphia. PA. US. vo 1. 27. No. 5. Sep. 1, 2009. pp. 435-445. XP026471172. ISSN: 0738-081X. DOI: DOI:10.1016/J.CLINDERMATOL.2009.05.006 [retrieved on Aug. 18, 2009] pp. 441-442.
Hanada K et al: "CERT-mediated trafficking of ceramide". Biochimica and Biophysica Acta. Molecular and Cell Biology Oflipids. Elsevier. Amsterdam. NL. vol. 1791. No. 7. Jul. 1, 2009 pp. 684-691. XP026174177. ISSN: 1388-1981. DOI: DOI:10.1016/J.BBALIP.2009.01.006 [retrieved on Jan. 22, 2009] the whole document.
International Search Report, dated Mar. 7, 2011, from corresponding PCT application.

* cited by examiner

METHOD FOR SCREENING ACTIVE AGENTS THAT STIMULATE THE EXPRESSION OF CERT TO IMPROVE THE SKIN'S BARRIER FUNCTION

The present invention relates to a method for screening an active agent intended for preventing or combating the cutaneous signs resulting from a non-pathological impairment of barrier function, comprising the selection of active agents that stimulate the expression of the ceramide transport protein CERT in cultured human keratinocytes.

The skin consists mainly of three layers, namely, starting from the uppermost layer, the epidermis, the dermis and the hypodermis.

The epidermis in particular consists of keratinocytes (predominantly), melanocytes (involved in pigmenting the skin) and Langerhans cells. Its function is to protect the body from the external environment and to ensure its integrity, and especially to halt the penetration of microorganisms or chemical substances, to prevent evaporation of the water contained in the skin and to constitute a barrier against external attack and especially against ultraviolet rays (UV).

To do this, keratinocytes undergo a process of proliferation and then of continuous directed maturation during which the keratinocytes located in the basal layer of the epidermis form, at the final stage of their differentiation, corneocytes, which are totally keratinized dead cells in the form of horny sheaths consisting of proteins and lipids such as epidermal ceramides. During this differentiation process, intercorneocytic epidermal lipids are also formed and then organized in the form of bilayers (lamellae) in the stratum corneum, and they participate, with the abovementioned horny sheaths, in the barrier function of the epidermis.

The lipid content of the stratum corneum consists of approximately 50% ceramides, 25% cholesterol, and 15% free fatty acids. Epidermal ceramides are synthesized by keratinocytes in a complex, multi-step cascade of reactions which begin in the endoplasmic reticulum (ER). Ceramides are transported from the ER to the Golgi apparatus for further modification to sphingomyelin through either vesicular or non-vesicular transport. Non-vesicular transport is the major mechanism. Sphingomyelin is then transported to lamellar bodies and excreted from the keratinocytes to be further processed in the stratum corneum, during terminal differentiation, into some of the epidermal ceramides which are then incorporated into the lamellar membrane structures that subserve the permeability barrier to water loss (Y. Uchida et al., *Journal of Lipid Research*, Vol. 41, 2071-2082, 2000).

The barrier function of the epidermis may, however, be perturbed under certain climatic conditions (for example under the effect of cold and/or the wind) or under the effect of stress or fatigue, especially, thus promoting the penetration of allergens, irritants or microorganisms. These external factors may lead to drying of the skin (the skin loses its permeability, becomes dehydrated and its transepidermal water loss increases), and sensations of heating or redness, and also to impair the radiance of the complexion and the suppleness of the skin. Impairment of the skin barrier may also promote the appearance of microchapping or microcracks.

Furthermore, a badly formed barrier, resulting from impaired proliferation and differentiation processes, no longer protects the skin against UV radiation or any other type of external attack. The UV rays penetrating the skin may then produce free radicals which may have a detrimental effect on various targets, such as activate collagenases and elastases which are responsible for the degradation of collagen and elastin, respectively, and thus for a decrease in skin elasticity and firmness and the formation of wrinkles.

To prevent or correct this phenomenon, it is known practice to apply to the skin cosmetic compositions containing hygroscopic agents, such as sugars or polyols, which are intended to take up the water present in the skin and thus to impede its evaporation. Use has also conventionally been made of fatty substances that allow an occlusive film to be formed on the skin, which contributes towards impeding the evaporation of water. Moreover, these compositions frequently incorporate active agents that act on one or more of the various biological targets involved either in skin turnover processes, in particular in keratinocyte differentiation, epidermal lipid synthesis and corneocyte cohesion, or in the endogenous synthesis of natural moisturizing factor (NMF) constituents of the skin, in particular in the synthesis of proteoglycans.

Examples of such active agents are especially α- and β-hydroxy acids, especially lactic acid, glycolic acid and salicylic acid; urea; and aminosulfonic compounds.

It is also known practice, to improve skin barrier function by applying onto skin an intermediate of the synthetic pathways, or precursor, for ceramides chosen from the sphinganine and sphingosine bases, such as 6-hydroxy-4-sphingenine (FR-2,811,556).

Similarly, it has also been proposed to act on some biological targets which increase the ceramide content of skin lipids, in order to improve skin barrier function. Among these targets, mention can be made of β-glucosidases, which have been shown to be stimulated by carbohydrates such as O-octanoyl-6'-maltose (WO 02/38110).

However, there always remains the need to propose novel cosmetic active agents for reinforcing the skin's barrier function to prevent and/or reduce the sensations of cutaneous discomfort, stinging, tautness, itching, sensations of heating or redness and/or the appearance of microchapping or microcracking and/or the loss of radiance of the complexion or dull complexion and/or the loss of suppleness of the skin and/or to improve the protection of the epidermis against UV.

In addition, given the ever-increasing search by consumers for natural products containing the fewest possible synthetic ingredients, and the increasingly burdensome regulatory constraints on compounds derived from the chemical industry, it would be desirable for these cosmetic active agents to be of plant origin.

Now, the Applicant has, to its credit, shown, unexpectedly, that it is possible to act on a novel biological target, namely the ceramide transporter CERT, by stimulating the expression of this protein, in order to combat impairment of the barrier function. The Applicant has also, to its credit, developed an appropriate screening test for selecting active agents such as plant extracts acting on this target, thus making it possible to satisfy the abovementioned needs.

The recently discovered CERT ceramide transport protein has elucidated a novel pathway to deliver ceramides synthesized in the ER to the Golgi for transformation into sphingomyelin (Hanada et al. *Nature* 426:803-809). The protein is identical in sequence, though not proposed function, to the Goodpasture antigen-binding protein (GPBP) splice variant GPBPΔ26. Mutation of CERT results in cells with significantly decreased sphingomyelin content. In *D. melanogaster* cells, CERT mutation resulted in changes in cellular membrane fluidity which resulted in enhanced damage from oxidative stress and reduced organism lifespan (Rao et al. *Proc. Nat. Acad. Sci. USA* 104:11364-11369). Exposure of cultured keratinocytes or ex vivo murine skin to UVB resulted in the inability of CERT to efficiently transport ceramide and further resulted in increased cell death (Charruyer et al. *J. Biol. Chem.* 283:16682-16692).

In order to improve ceramide transport, it has been proposed in EP 1 652 530 to administer compositions comprising a drug which is a protein having the amino acid sequence of CERT. This drug may be used as an antitumor agent, an anti-inflammatory agent, an organoregenesis agent, an anti-infective agent, or a distribution promoting agent used for cosmetics. In the latter case, the drug may be applied onto skin so as to improve its water retention.

To the Applicant's knowledge, however, cosmetic active agents that stimulate the expression of CERT have never been disclosed.

Moreover, it has never been suggested that CERT expression could be stimulated in keratinocytes with a view to improving epidermal barrier function.

Furthermore, the Applicant has shown that the expression of CERT decreased with age. Thus, compounds that stimulate the expression of CERT could also be useful to prevent and/or treat the signs of skin ageing.

One subject of the present invention is thus a method for screening active agents, which are able to prevent or combat the cutaneous signs resulting from non-pathological impairment of barrier function, comprising the following steps:
a) treating a sample of cultured keratinocytes from a human donor with an active agent, such as a botanical extract;
b) quantifying the expression of CERT in said treated sample, relative to the same cell sample which has not been treated;
c) selecting the active agents that provide for an increase in the expression of CERT relative to the untreated sample.

In this method, the quantification of the expression of CERT may be performed by real-time RT-PCR on cultured keratinocytes. In this situation, step c) preferably comprises selecting the active agents that provide for at least a 1.7 fold increase in the gene expression level of CERT, compared to the untreated sample.

Alternatively, the quantification of the expression of CERT may be performed by Western blotting on cultured keratinocytes. In such a case, step c) advantageously comprises selecting the active agents that provide for a CERT protein level which is at least 120% of that expressed by the untreated sample.

However, any other means for quantifying the expression of CERT, for instance by quantifying the production either of messenger RNA of CERT or of CERT protein, may be used without departing from this invention.

The active agents that may be selected according to the invention are advantageously botanical extracts, i.e. active agents obtained by extraction, using any type of solvent, of any part of a plant such as bark, wood, roots, rhizomes, stalks, leaves, fruit or flowers, for example.

In general, the extraction may be performed on fresh or dried parts of the plant, optionally chopped or ground, in the usual manner. The extraction is generally performed by immersing or gently shaking in one or more polar or apolar solvents or a mixture thereof, at temperatures ranging, for example, from room temperature to 100° C. and advantageously from 30 to 70° C., for a time of about 30 minutes to 12 hours and preferably from 1 to 8 hours. The resulting solution is then preferably filtered so as to remove the insoluble substances of the plant. The solvent is also, where appropriate, removed if it is a volatile solvent, for instance ethanol, methanol or isopropanol.

Alternatively, the botanical extract may be prepared by extraction using a supercritical fluid such as carbon dioxide.

According to still another embodiment, it may be obtained by hydro-distillation, i.e. according to a method including a step for extracting vapour distillation residues, after elimination of the essential oils, by using a polar organic solvent having a polarity index greater than 3.5, possibly mixed with an apolar organic solvent having a polarity index less than 1.

All these extraction methods are common in the field of plant extracts and a person skilled in the art is capable of adjusting the reaction parameters thereof on the basis of his general knowledge.

After this extraction step, a botanical extract is obtained, which may then be subjected to a decolorizing step, especially using active charcoal in the presence of a solvent. The weight of active charcoal is preferably between 0.5% and 50% of the weight of the extract. One or more solvents chosen from water, $C_1$-$C_4$ alcohols such as methanol, ethanol or isopropanol, polar organic solvents such as propylene glycol or dipropylene glycol, or any other solvent that is common in the field, may especially be used. The volatile solvents may then be removed under reduced pressure.

The skilled person will be able to prepare various botanical extracts, for example by varying the plants and solvents used. Alternatively, plant extracts that are commercially available may be used in this invention. These extracts should then be subjected to screening tests as described above and in the following examples, so as to determine whether any of these botanical extracts provides for an increase in the gene or protein expression level of CERT and may thus be selected according to this invention.

When it passes the above screening test(s), the active agent selected according to the invention may be used for cosmetic purposes, to prevent or combat the cutaneous signs resulting from non-pathological impairment of the barrier function. The above-mentioned method may thus be used for selecting agents capable of protecting skin against signs of dryness such as: skin roughness, the loss of radiance of the complexion and/or the loss of suppleness of the skin; for protecting skin from the external environment, especially from the damaging effects of UV rays or from the penetration of toxins, drugs, and chemical substances; and for reducing oxidant load in the skin, when applied topically to human skin.

The barrier integrity may especially be measured by corneometry, according to usual techniques that are well known to those skilled in the art.

As a variant, the screening method of this invention may be used for selecting agents capable of preventing skin photoaging, when applied topically to human skin.

The active agent selected according to the invention, or the composition containing same, are preferably applied to non-pathological dry skin and/or aged skin. They may advantageously be applied to the skin of the face, the neck and possibly the neckline or, as a variant, to any part of the body.

In this regard, the active agent is included in the cosmetic composition, for instance in a proportion of from 0.00001% to 10% by weight, preferably in a proportion of from 0.0001% to 5% by weight and more preferably in a proportion of from 0.001% to 1% by weight relative to the total weight of the composition.

The composition containing this active agent may be applied in the morning and/or in the evening, to the entire face, the neck and optionally the neckline or even the body.

This composition generally comprises, besides the active agent described previously, a physiologically acceptable and preferably cosmetically acceptable medium, i.e. a medium that is suitable for use in contact with human skin without any risk of toxicity, incompatibility, instability or allergic response and especially that does not cause any sensations of discomfort (redness, tautness, stinging, etc.) that are unacceptable to the user.

This medium generally contains water and optionally other solvents such as ethanol.

The composition containing the active agent selected according to the invention may be in any form that is suitable for topical application to the skin and in particular in the form of an oil-in-water, water-in-oil or multiple emulsion (W/O/W or O/W/O), which may optionally be microemulsions or nanoemulsions, or in the form of an aqueous dispersion, a solution, an aqueous gel or an anhydrous composition. It is preferable for this composition to be in the form of an oil-in-water emulsion.

This composition is preferably used as a care and/or cleansing product for facial and/or bodily skin and it may especially be in the form of a fluid, a gel or a mousse, conditioned, for example, in a pump-dispenser bottle, an aerosol or a tube, or in the form of cream conditioned, for example, in a jar. As a variant, it may be in the form of a makeup product and in particular a foundation or a loose or compact powder.

It may contain various adjuvants, such as at least one compound chosen from:
  oils, which may be chosen especially from: linear or cyclic, volatile or non-volatile silicone oils, such as polydimethylsiloxanes (dimethicones), polyalkylcyclosiloxanes (cyclomethicones) and polyalkylphenylsiloxanes (phenyl dimethicones); synthetic oils such as fluoro oils, alkylbenzoates and branched hydrocarbons such as polyisobutylene; plant oils and especially soybean oil or jojoba oil; and mineral oils such as liquid petroleum jelly;
  waxes such as ozokerite, polyethylene wax, beeswax or carnauba wax;
  silicone elastomers obtained especially by reaction, in the presence of a catalyst, of a polysiloxane containing at least one reactive group (especially hydrogen or vinyl) and bearing at least one alkyl group (especially methyl) or phenyl, in a terminal and/or side position, with an organosilicone such as an organohydrogeno-polysiloxane;
  surfactants, preferably emulsifying surfactants, whether they are nonionic, anionic, cationic or amphoteric, and in particular fatty acid esters of polyols such as fatty acid esters of glycerol, fatty acid esters of sorbitan, fatty acid esters of polyethylene glycol and fatty acid esters of sucrose; fatty alkyl ethers of polyethylene glycol; alkylpolyglucosides; polysiloxane-modified polyethers; betaine and derivatives thereof; polyquaterniums; ethoxylated fatty alkyl sulfate salts; sulfosuccinates; sarcosinates; alkyl and dialkyl phosphates, and salts thereof; and fatty acid soaps;
  co-surfactants such as linear fatty alcohols and in particular cetyl alcohol and stearyl alcohol;
  thickeners and/or gelling agents, and in particular crosslinked or non-crosslinked, hydrophilic or amphiphilic homopolymers and copolymers, of acryloylmethylpropanesulfonic acid (AMPS) and/or of acrylamide and/or of acrylic acid and/or of acrylic acid salts or esters; xanthan gum or guar gum; cellulose derivatives; and silicone gums (dimethiconol);
  organic screening agents, such as dibenzoylmethane derivatives (including butylmethoxydibenzoyl-methane), cinnamic acid derivatives (including ethylhexyl methoxycinnamate), salicylates, para-aminobenzoic acids, β,β'-diphenyl acrylates, benzophenones, benzylidenecamphor derivatives, phenylbenzimidazoles, triazines, phenyl-benzotriazoles and anthranilic derivatives;
  inorganic screening agents, based on mineral oxides in the form of coated or uncoated pigments or nanopigments, and in particular based on titanium dioxide or zinc oxide;
  dyes;
  preserving agents;
  fillers, and in particular powders with a soft-focus effect, which may be chosen especially from polyamides, silica, talc, mica and fibers (especially polyamide fiber or cellulose fiber);
  sequestrants such as EDTA salts;
  fragrances;
  and mixtures thereof, without this list being limiting.

Examples of such adjuvants are especially mentioned in the CTFA dictionary (International Cosmetic Ingredient Dictionary and Handbook published by The Cosmetic, Toiletry and Fragrance Association, 11th edition, 2006), which describes a wide variety, without limitation, of cosmetic and pharmaceutical ingredients usually used in the skincare industry, that are suitable for use as additional ingredients in the compositions according to the present invention.

The composition containing the active agent selected according to the invention may also provide additional benefits, including calmative or anti-inflammatory activity, bleaching or depigmenting activity, anti-aging activity and/or cleansing activity.

This composition may also comprise active agents other than those that stimulate the expression of CERT, and in particular at least one active agent chosen from: keratolytic agents and in particular α-hydroxy acids such as glycolic acid, lactic acid and citric acid, and esters or salts thereof; β-hydroxy acids such as salicylic acid and derivatives thereof; agents for increasing keratinocyte differentiation and/or cornification, either directly or indirectly by stimulating, for example, the production of β-endorphins, such as extracts of *Thermus thermophilus* or extracts of bean husks of *Theobroma cacao*, water-soluble extracts of corn, peptide extracts of *Voandzeia substerranea* and niacinamide; epidermal lipids and agents for increasing the synthesis of epidermal lipids, either directly or by stimulating certain β-glucosidases that modulate the deglycosylation of lipid precursors such as glucosyl ceramide to ceramides, such as phospholipids, ceramides, lupin protein hydrolyzates and dihydrojasmonic acid derivatives; humectants, such as polyols and in particular glycerol, glycosaminoglycans such as hyaluronic acid, sugars and alkyl esters thereof, amino acids such as glycine, arginine, histidine, alanine, threonine, lysine, glutamic acid, taurine, proline, serine and derivatives thereof, pyrrolidonecarboxylic acid (PCA) and salts thereof, urea and derivatives thereof, ectoin, glucosamine, creatine, choline, betaine, mineral salts such as chlorine, sodium, potassium, calcium, magnesium, zinc, manganese or phosphate salts and humectant synthetic polymers such as methacryloyloxyethylphosphorylcholine homopolymers and copolymers, and glyceryl (meth)acrylate homopolymers and copolymers; antioxidants and/or free-radical scavengers and/or anti-pollution agents, such as tocopherol and esters thereof, ascorbic acid and the alkyl and phosphoryl esters thereof and certain extracts of plants or algae and in particular of *Thermus thermophilus*; and mixtures thereof, without this list being limiting.

The combination of active agents that stimulate the expression of CERT with one or more of the agents described above makes it possible advantageously to combine in the same formula the effects of these two types of active agent and thus to obtain maximum and long-lasting protection of the skin.

The invention will now be illustrated by the non-limiting examples that follow.

EXAMPLES

Example 1

Test for Screening Active Agents by Western Blotting

Protocol:

A *Vanilla planifolia* extract was prepared as described in Example 1 of WO 2007/034042.

The effect of a botanical extract on the expression of CERT protein is evaluated on keratinocytes.

Keratinocytes derived from neonatal foreskins (Cascade Biologics/Invitrogen, Portland, Oreg., USA) are inoculated in 6-well plates and cultured in keratinocyte growth culture medium (Epilife, Invitrogen, CA, USA), i.e. a modified culture medium supplemented with Epilife defined growth supplement (EDGS).

After culturing for 24 hours in an incubator at 37° C., the almost confluent cells are washed with PBS buffer (Invitrogen) and incubated with specific basic medium (Epilife, Invitrogen) containing the extract to be tested, for 24 hours and in triplicate, at increasing concentrations. Cytotoxicity of the extract is determined prior to determining its activity.

To quantify the expression of CERT protein in a treated sample relative to an untreated sample, Western blotting (WB) is used. Cells incubated as described above are lysed and the extracted proteins are separated by SDS-PAGE. Following electrophoresis, proteins are transferred to a PVDF membrane which is probed with anti-CERT antibody (Bethyl Laboratories, TX, USA). The results are normalized to the amount of total protein in each sample. The results are expressed in terms of the percent (%) increase or decrease of expression of the target protein CERT in the treated sample versus the untreated control.

The total protein content is quantified using the MicroBCA kit (Thermo Scientific, IL, USA).

The positive results are confirmed using cells from at least two different donors.

Results:

The results are given in Table 1 below:

TABLE 1

|  | Concentration | Stimulation of CERT Protein | Average deviation |
|---|---|---|---|
| Untreated keratinocytes | — | 100.0% | 0.0% |
| *Vanilla planifolia* extract | 0.02% | 130.3% | 5.0% |

It emerges from this test that *Vanilla Planifolia* extracts make it possible to stimulate the expression of CERT protein in normal human keratinocytes and may thus be used to improve or restore skin barrier function.

Example 2

Test for Screening Active Agents by RT-PCR

Protocol:

The effect of two active agents on the expression of the mRNA of CERT was evaluated in keratinocytes.

Keratinocytes derived from neonatal foreskins (Cascade Biologics/Invitrogen, Portland, Oreg., USA) are inoculated in 6-well plates and cultured in keratinocyte growth culture medium (Epilife, Invitrogen), i.e. a modified culture medium supplemented with EDGS.

After culturing for 24 hours in an incubator at 37° C., the 70%-80% confluent cells are washed with PBS buffer (Invitrogen) and incubated with basic medium (Epilife, Invitrogen) containing the active agent to be tested, for 24 hours and in triplicate, at increasing concentrations. After studying the cytotoxicity of the active agent, its activity is evaluated.

To quantify the expression of CERT messenger RNA in a treated sample relative to an untreated sample, first the RNA is isolated using the RNeasy reagent kit (Qiagen, CA, USA) and then quantified using the QuantIt kit (Invitrogen). Reverse transcription is performed using the gene Amp RNA PCR kit (Applied Biosystems) according to the manufacturer's recommendations.

The real-time PCR measurement is performed using the iCYCLER IQ machine (Bio-Rad, CA, USA) with Taqman probes. The PCR primers are obtained from Applied Biosystems (Applied Biosystems, CA, USA). In all the tests, the cDNA is amplified using a standardized program. Each sample is charged with Taqman master-mix, Taqman primers, and water. The final amount of cDNA per reaction corresponds to 75 ng of total RNA used for the reverse transcription.

The results are normalized relative to the expression of a housekeeping gene in these samples and corrected as regards the differences in efficacy of PCR. The housekeeping gene used here was RPLPO. The relative quantification of the expression of the target gene is performed using the Pfaffl mathematical model (Pfaffl, MW, Nucleic Acids Res. 29(9), p. E45, 2001). The results are expressed in terms of the number of times of increase or of decrease of expression of the target gene CERT in the treated sample.

Results:

The results are given in Table 2 below:

TABLE 2

|  | Concentration | Stimulation of CERT mRNA | Standard deviation |
|---|---|---|---|
| Untreated keratinocytes | — | 1.0 | 0.0 |
| Lipoic acid | 0.0005% | 2.0 | 0.3 |
| Resveratrol | 0.0005% | 2.4 | 0.3 |

It emerges from this test that the active agents tested make it possible to stimulate the expression of CERT protein in normal human keratinocytes and may thus be used to improve or restore skin barrier function.

Example 3

Assessment of the Expression of CERT with Age

Protocol:

The variation in expression of the CERT protein was evaluated by immunohistochemistry (IHC), on paraffin-embedded skin samples from donors of various age groups (Cybrdi, MD, USA and Tissue Array Networks, MD, USA). Staining was performed on 6 µm sections from donors in 4 age groups (20-30 weeks old, 28-35 years old, 39-49, and 50-69 years old), with anti-CERT antibodies (Bethyl Laboratories, TX, USA) and secondary antibodies (Lab Vision, CA, USA). The staining was visualized using the AEC system (Lab Vision). Staining was assessed on 2-6 images each from 3-6 donors in each age group by doing a blind visual assessment of the intensity and extent of staining using a scale from 1 to 5 (1=least intense, 5=most intense). Mean values of ratings were compared for significance using the unpaired t-test.

Results:

Evaluation of CERT staining in young adult skin (28-35 yrs old) showed intense cytoplasmic staining in the epidermis which translated to a rating of 4.63 (±0.5). The intensity of staining then visibly decreased in sections of elder donor skin (39-49) and especially at 50-69 years of age, where staining intensity was rated 3.06 (±0.66). This demonstrates that expression of CERT protein is significantly diminished with increasing age (P<0.0001).

Example 4

Cosmetic Composition

The following composition may be prepared in a manner that is conventional for those skilled in the art. The amounts indicated below are expressed as weight percentages. The ingredients in upper case are identified in accordance with the INCI name.

| | |
|---|---|
| Tetrasodium EDTA | 0.05% |
| POLYGLYCERYL METHACRYLATE & PROPYLENE GLYCOL[1] | 5.00% |
| Glycerol | 6.00% |
| Aqueous-phase gelling agents | 5.50% |
| Nonionic emulsifiers | 4.00% |
| Cetearyl alcohol | 2.00% |
| Emollients | 17.00% |
| Tocopheryl acetate | 0.50% |
| Preserving agents | 2.20% |
| Botanical extract[2] | 0.05% |
| Sodium hyaluronate | 5.00% |
| Fragrance | qs |
| Dyes | qs |
| Water | qs 100.00% |

[1]LUBRAJEL MS ® from Guardian Laboratories
[2]obtained by screening various plant extracts on the test disclosed in Example 1 or 2

This composition, in the form of an oil-in-water emulsion, may be applied daily, morning and/or evening, to facial skin to moisturize it and make it supple, smooth and luminous.

The invention claimed is:

1. A method for screening active agents, which are able to increase expression of mRNA of CERT in keratinocytes from a human donor, comprising the following steps:
   a) treating a sample of cultured keratinocytes from a human donor with an active agent;
   b) quantifying the expression of mRNA of CERT in said treated sample, relative to an untreated sample of said cultured keratinocytes which has not been treated;
   c) selecting the active agents that provide for an increase in the expression of mRNA of CERT relative to the untreated sample.

2. The method according to claim 1, wherein quantification of the expression of mRNA of CERT is performed by RT-PCR.

3. The method according to claim 2, wherein step c) further comprises selecting the active agents that provide for at least a 1.7 fold increase in the gene expression level of CERT, compared to an untreated sample where expression is at 1.

4. The method according to claim 1, wherein step c) further comprises selecting the active agents that provide for a CERT protein level, which is at least 120% of that expressed by the untreated sample.

5. The method according claim 1, wherein the active agent is a botanical extract.

* * * * *